United States Patent [19]

Calbet Benach et al.

[11] Patent Number: 5,728,141
[45] Date of Patent: Mar. 17, 1998

[54] ELECTROTHERAPY APPARATUS

[75] Inventors: José Calbet Benach; Epifanio Jodra Hernandez, both of Barcelona, Spain

[73] Assignee: Indiba, S.A., Barcelona, Spain

[21] Appl. No.: 699,856

[22] Filed: Aug. 20, 1996

Related U.S. Application Data

[63] Continuation of Ser. No. 424,120, Apr. 19, 1995, abandoned.

[30] Foreign Application Priority Data

May 4, 1994 [ES] Spain ................................. 9400929

[51] Int. Cl.$^6$ .................................................. A61N 1/06
[52] U.S. Cl. ............................ 607/98; 607/148; 128/644
[58] Field of Search ...................... 607/98, 99, 146–149; 128/644

[56] References Cited

U.S. PATENT DOCUMENTS 1,657,149  1/1928  Catlin .................................. 607/148
4,846,196  7/1989  Wiksell et al. .......................... 607/99

FOREIGN PATENT DOCUMENTS 2242132  9/1991  United Kingdom ................ 607/99

*Primary Examiner*—Robert L. Nasser
*Attorney, Agent, or Firm*—Jacobson, Price, Holman & Stern, PLLC

[57] ABSTRACT

A relatively high-frequency electric current is generated, to be applied to the human body by means of one active and one passive electrode. It is distinct because, in order to raise the temperature of the human body in a local sense to 45°–46° C., it comprises a return electrode consisting of a metal plate and an active electrode, likewise metal, of smaller dimensions than the return electrode. The difference in dimensions between the two electrodes, placed facing on either side of the body region to be treated, brings about an increase in the impedances which, combined with the power frequency amplifier generator, brings about the required rise in temperature for treatment at local level.

4 Claims, 1 Drawing Sheet

ELECTROTHERAPY APPARATUS

This is a continuation of application Ser. No. 08/424,120, filed Apr. 19, 1995 which was abandonded upon the filing hereof;

BACKGROUND OF THE INVENTION

The invention referred to herein consists of an electrotherapy apparatus, basically designed for the treatment of parts of the body affected by neoplasiae and other phenomena originated by abnormal cell growth. An expedient application of this apparatus is in the selective destruction of cancerous cells, which occurs in a short period of time by virtue of the functioning of the therapeutic apparatus in question, without affecting the healthy tissue that are revitalised. The apparatus, in addition, has other utilities and possibilities.

Technology is such that there are currently other recognised electrotherapeutic devices designed to produce hyperthermia, i.e., the local heating of cellular tissue in certain parts of the body affected by neoplasiae and similar afflictions. Such instruments, based always on applying high-frequency currents, have various disadvantages that have been eliminated in the design of the device hereby patented.

One recognised form of hyperthermia apparatus for electrotherapy employs two insulated, symmetrical metal plates subjected to very high frequency current (varying between 10–200 MHz), the body acting as dielectric. This method has the disadvantage of producing general rather than selective heating and is therefore inefficient as regards the intended effect, and has the additional disadvantage of needing very high power levels in order to reach the required temperature.

Another recognised method of electrotherapy originates hyperthermia by means of two, similarly symmetrical, but non-insulated metal plates, and in this case the patient's body acts as a resistor. The disadvantage of this method is likewise the need to employ a high power input in order to achieve the desired effect and symmetry in obtaining it.

A third method of applying high-frequency currents in hyperthermal therapy consists of employing dipole aerials to which very high frequencies are applied, in the order of 200 to 800 MHz, which requires constant cooling at epidermic level and special protection for those performing the treatment due to the high frequency that must be used.

SUMMARY OF THE INVENTION

The electrotherapy apparatus constituting the invention herein is based on the employment of two metal plates with special characteristics that are applied to the relevant parts of the body, based on the latter's geometrical shape and surface.

The electrode that is active or applies the high frequency is made of stainless steel metal, and is shaped appropriately according to the anatomy of the region of the body to which it is applied, although its surface area should correspond to the area on which treatment is to be carried out.

The return electrode consists of a metal plate of a sufficient surface area to avoid local overheating and substantially greater in comparison to the active electrode. It must be of a rustproof, polished material, with no sharp edges and of an adequate surface area.

The difference in dimensions, i.e., the surfaces of application, between the active electrode and that of the return electrode are fundamental in the practice of therapeutic methods utilising the invented apparatus herein, given that the greater impedance or resistance to the current occurs in the regions with a smaller contact surface. It consists, as a certain intensity of current circulates between the two electrodes, of a drop in tension occurring in the region that is closest to the active electrode. The magnitude is such that, as it is multiplied by the general intensity, it will produce greater dissipation and therefore an increase in temperature (not heat) at depth, based on the power applied. The latter may be in the order of 300 watts and, in the circumstances described, a temperature of from 45° to 46° C. at a deep level is reached, in a time of between two to four minutes according to the power selected, without affecting the epidermic area of the region under treatment. The latter will maintain normal body temperature and may even drop due to the effect of absorption of some body heat in the region of the stainless steel metal plate comprising the active electrode. Meanwhile internally, at a depth of a few centimeters, the body tissue may be some 8° to 10° C. above the level of the temperature of the region where the active electrode is in contact.

The difference in surface area between the two electrodes and the sharing of electric current intensity between them is distinct, therefore, to this invention.

The electrotherapy apparatus, the subject of the invention herein, conventionally comprises a high-frequency oscillator, which operates at a frequency value of around 600 kilohertz, although it can function for an interval at between 300 kilohertz and 1 megahertz, approximately. The two-channel oscillator stage follows two previous amplifier blocks which increase the intensity of the signals generated and are followed by amplifiers that respectively charge the final amplification stage, whose output provides the power, at approximately 300 watts as mentioned previously, to operate at an impedance of some 240 ohms, corresponding on average to the value defined by the human body.

However this circuit may be designed in another way. Even when the active electrode is applied statically, in some cases it can be applied by moving it around the area to be treated in order to achieve effect on a wider area (including ganglia). Furthermore, raising and lowering the temperature intermittently at various points in the treatment region, helps in the attack on the cancerous cells.

DESCRIPTION OF THE PREFERRED EMBODIMENTS

In order to facilitate the explanation, a diagram has been enclosed with the description herein showing an, illustrative rather than limiting, example of a case method of the active part of the electrotherapy apparatus performing according to the principles of the claims.

Figure 1:
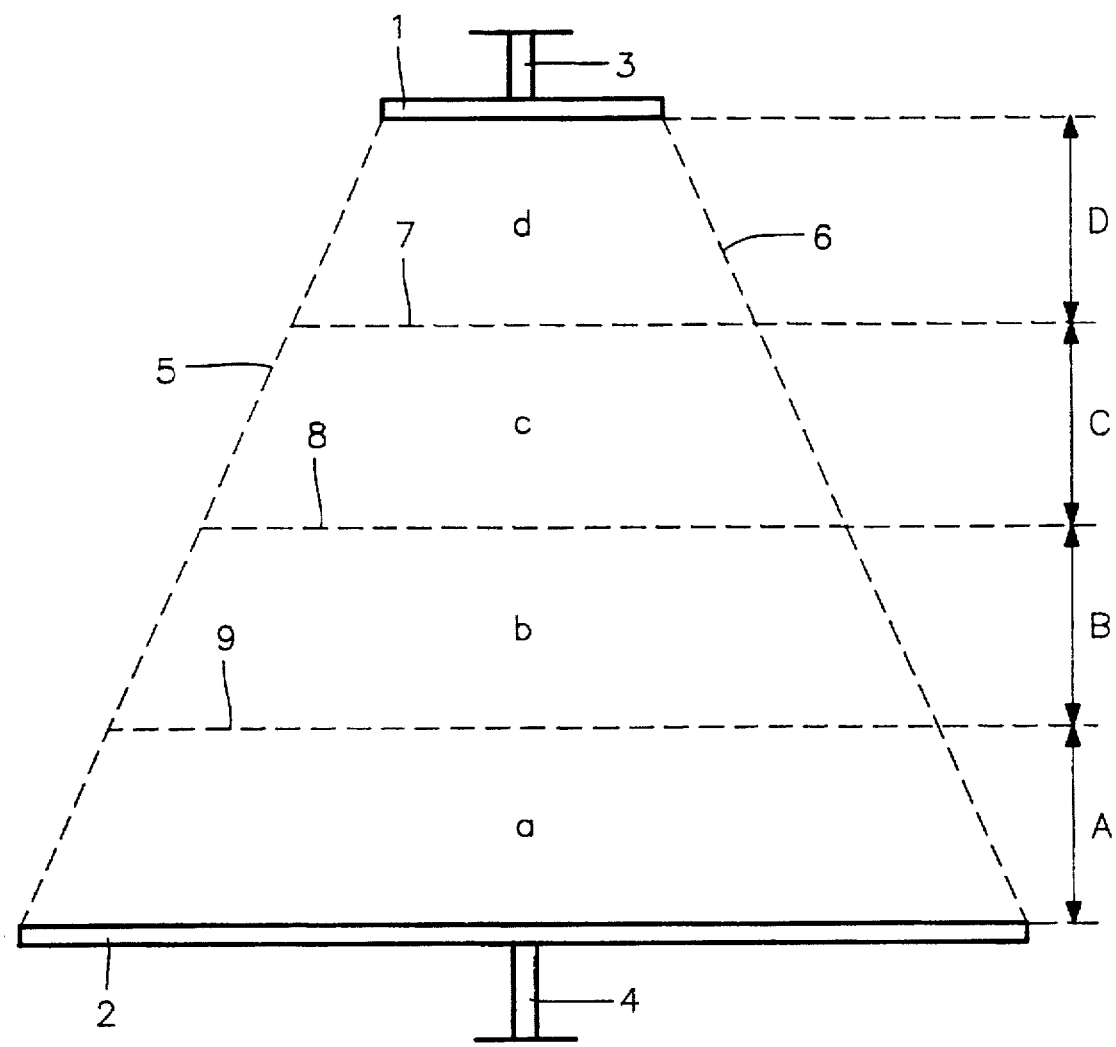
FIG. 1 is a schematic drawing depicting operation of a preferred electrotherapy apparatus in accordance with the present invention.

FIG. 1 outlines the two working electrodes, viewed in profile and on the same ideal axis, the lines indicating the theoretical areas of resistance sharing and consequently the induced tension resulting from the circulation of a high frequency electric current applied at a certain tension and power to the main electrode.

Figure 2:
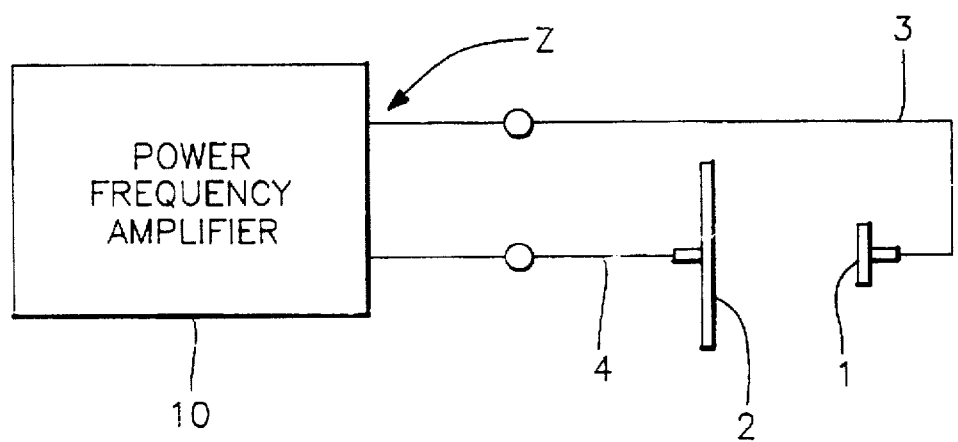
FIG. 2 is a schematic block diagram illustrating various elements of a preferred electrotherapy apparatus in accordance with the present invention.

In the diagram the application electrode 1, consists of a relatively small metal plate, the large plate 2 is the return electrode, and shunts 3 and 4 connect both electrodes to the output circuit of the apparatus. The oblique lines 5 and 6 limit the trapezial zones determined by transversal lines 7, 8 and 9, which delimit the area of partial resistance and corresponding power applied. As an example of power concentration, the zones marked with letters a, b, c and d would correspond to an obtention of 50, 100, 200, and 650 ohms, impedance and A, B, C and D would correspond to 12.5, 25, 50 and 162.5 watts of power. The connection of the electrodes 1, 2 to a power frequency amplifier 10 having a suitable output impedance at Z is illustrated in FIG. 2.

In an expedient implementation of the electrotherapy apparatus described, the oscillator stage is made up of an integrated circuit following a prior-transfer transistor amplifier with a charge amplifier for the output stage, all two-channel, with an output transformer that transmits the current to the connecting terminals for the conductors 1, 2 linking the apparatus to the electrodes.

Lights are employed, indicating the machine's state of functioning and operating conditions, fed by its own power circuit, distinct from the circuit for the polarization of the transistors and integrated circuits. It is equipped with fans to dispel the heat generated by the output transistors. There are control devices that regulate maximum consumption when the machine is functioning at high power and no load, in order to protect the output transistors.

A digital timer allows the duration of treatment to be measured and regulated. An automatic circuit that detects accidental disconnection of one of the plates, stopping current passing through one of the primary symmetrical windings of the output transformer, produces a visible and audible alarm signal.

We claim:

1. Electrotherapy apparatus for applying a relatively high frequency electric current to the human body, said apparatus comprising:

a power frequency amplifier; and an active electrode and a return electrode for placement on opposite sides of a body part to be treated, said active electrode and said return electrode being connected at least indirectly to the power frequency amplifier, said active electrode and said return electrode being metal, substantially non-deformable when in use and having a generally planar configuration which facilitates non-invasive placement of the electrodes in contact with an outer layer of skin, said active electrode having smaller dimensions than the return electrode so as to provide, between the active electrode and the return electrode, higher impedance near the active electrode than there is near the return electrode, which, combined with the power frequency amplifier and a suitable output impedance of the power frequency amplifier, brings about a desired rise in temperature for treatment at a local level within the body part.

2. The apparatus according to claim 1, wherein said power frequency amplifier is configured and said active and return electrodes are arranged so as to locally raise the temperature of the body part to 45°–46° C.

3. The apparatus according to claim 1, wherein said power frequency amplifier is configured so as to generate electrical currents having frequencies between 300 KHz and 1 MHz.

4. The apparatus according to claim 1, wherein the active electrode is movably arranged to facilitate movement over said body part to be treated.

* * * * *